United States Patent [19]

Baldwin et al.

[11] Patent Number: 5,716,360
[45] Date of Patent: Feb. 10, 1998

[54] PATELLA RECESSION INSTRUMENT AND METHOD FOR ANATOMICALLY-SHAPED PATELLAR PROSTHESES

[75] Inventors: James L. Baldwin, Portland, Oreg.; James M. Freid; Steven I. Whitlock, both of Austin, Tex.; Mark L. Rehmann, Pflugerville, Tex.

[73] Assignee: U.S. Medical Products, Austin, Tex.

[21] Appl. No.: 497,537

[22] Filed: Jun. 30, 1995

[51] Int. Cl.$^6$ .................................................... A61B 17/56
[52] U.S. Cl. ................................ 606/80; 606/79; 606/87; 606/88
[58] Field of Search ............................. 606/88, 87, 80

[56] References Cited

U.S. PATENT DOCUMENTS

| | | | |
|---|---|---|---|
| 5,129,907 | 7/1992 | Heldreth et al. | 606/80 |
| 5,129,908 | 7/1992 | Petersen | 606/88 |
| 5,284,482 | 2/1994 | Mikhail | 606/87 |
| 5,342,364 | 8/1994 | Mikhail | 606/88 |
| 5,417,695 | 5/1995 | Axelson, Jr. | 606/87 |
| 5,486,177 | 1/1996 | Mumme et al. | 606/88 |
| 5,520,692 | 5/1996 | Ferrante | 606/88 |
| 5,536,271 | 7/1996 | Daly et al. | 606/88 |

OTHER PUBLICATIONS

Dow Corning Wright, Whiteside Ortholoc Modular Knee System, Apr. 1990.
Johnson & Johnson Orthopaedics, Modularity In a Simple and Complete System P.F.C. Modular Total Knee System, 1989.
DePuy, LCS Total Knee System with Porocoat, 1989.
Zimmer, Inc., Surgical Technique for Preparation of the Patella Using the Zimmer Patella Reamer, 1990–1991, pp. 1–19.
Dow Corning Wright, Whiteside Ortholoc Modular Knee System, pp. 24–27.
Aaron A. Hofmann, M.D., Intermedics Orthopedics, Inc., The Intermedics Natural–Knee System with Cancellous–Structured Titanium, copyrighted Apr. 1992, pp. 23,24.

*Primary Examiner*—Michael Buiz
*Assistant Examiner*—Julian W. Woo
*Attorney, Agent, or Firm*—Schaffer & Culbertson; Russel D. Culbertson

[57] ABSTRACT

A patella recession instrument (10) and method provides a guide for producing an oval, tri-oval, or elliptically shaped recess on the posterior surface of the osteotomized patella for receiving a similarly shaped backing portion of a patellar implant. The apparatus includes a guide bushing (12) and a bushing positioning mechanism (14) for securing the bushing against the posterior of the osteotomized patella, with a guide opening (54) formed through the bushing covering the total area to be recessed. A reamer guide structure, which may be a separate structure (16) received in the bushing guide opening (54) or integrally formed with the bushing (12), receives one or more rotary reamer tools (18) in a plurality of reaming positions. The cutting face (80) of the rotary reamer tool (18) in each different reaming position covers a different portion of the total area to be recessed. The recession method includes securing the guide bushing (12) in the proper operating position against the patella, sequentially positioning the cutting face (80) of the reamer tool (18) or tools in the plurality of different reaming positions, and operating the tool or tools to produce a series of intermediate recesses that combine to approximate the total area to be recessed.

20 Claims, 8 Drawing Sheets

PATELLA RECESSION INSTRUMENT AND METHOD FOR ANATOMICALLY-SHAPED PATELLAR PROSTHESES

BACKGROUND OF THE INVENTION

This invention relates to total knee arthroplasty and particularly to an apparatus and method for recessing a patella to receive an anatomically shaped patellar prosthesis.

Total knee replacement or arthroplastic surgery includes providing new articulating surfaces on the posterior surface of the patella. The surgical procedure includes removing or resecting the natural articulating surface on the posterior side of the patella and replacing the surface with a patellar implant having an artificial articulating surface.

Prior patellar prostheses comprised a non-anatomically shaped button or round implant positioned on the posterior surface of the patella after the patella was resected and resurfaced or osteotomized to the insertion of the quadriceps and infrapatellar tendons. To duplicate the natural articulating surface, the round non-anatomically shaped implant had to be moved medially or medialized on the posterior surface of the patella. However, due to the round shape of the implant as compared to the oblong or elliptical shape of the resected patellar surface, the medialized positioning of the round implant left exposed resected bone on the lateral facet of the patella.

Another problem with prior patellar implants was in concealing the metal endoskeleton of a metal backed implant and in stabilizing the prosthesis against side loading and anterior/posterior and medial/lateral forces. In order to stabilize the implant, the surface of the patella had to be recessed to form a pocket for receiving the implant, or a feature formed on the back of the implant.

In response to the problems associated with the round, non-anatomically shaped patellar implant, a generally elliptical or oval shaped medialized implant has been developed. However, there has been no apparatus or method for accurately recessing the patella to receive such anatomically shaped implants. Prior elliptical or oval patellar implants were not designed to be received in a recess but were simply affixed over the resected patellar surface using pegs extending into the patella or a suitable cement, or both.

SUMMARY OF THE INVENTION

It is therefore a broad object of the invention to provide an apparatus and method for overcoming the above-described problems and others associated with implanting a patellar prosthesis in total knee arthroplasty. More particularly, it is an object of the invention to provide an apparatus and method for accurately producing a recess in the posterior surface of a patella for receiving an anatomically shaped patellar implant.

In order to accomplish these objects, an apparatus according to the invention includes a guide bushing that may be secured to the posterior surface of an osteotomized patella in an operating position. The guide bushing includes a guide opening which covers the total area of the patella to be recessed when the guide bushing is in the operating position. Guide means associated with the guide bushing allow at least one rotary reamer tool to be fixed in a plurality of reaming positions within the guide opening. The rotary reamer tool or tools in each different reaming position cover a different portion of the total area to be recessed and these different portions of the total area to be recessed combine to approximate the total area to be recessed. The total area to be recessed may be oval, tri-oval, elliptical, or any other desired oblong shape that approximates the anatomical shape of the osteotomized patella.

The guide means associated with the guide bushing operates to form a guide for positioning the rotary reamer tool or tools in the different reaming positions. Although each rotary reamer tool can make only a round recess, the overlapping round recess areas created by the rotary reamer tool or tools in the plurality of different positions within the guide bushing combine to approximate the desired oval or other oblong shape. The ability to accurately create an oblong recess in the osteotomized surface of the patella during total knee arthroplasty allows the implant to include a backing or endoskeleton that may be pressed into the desired oblong recess to provide superior fixation to the patella and stabilization against forces to which the implant will be subjected after implantation. The backing or endoskeleton which is stabilized in the recess can support a medialized articulating surface that approximates the original anatomical shape of the posterior surface of the patella.

The reamer guide means may be integrally formed with the guide bushing or comprise a separate guide member adapted to be received in the guide bushing opening. Where the reamer guide means is integrally formed with the guide bushing, the reamer guide means comprises a guide surface forming the wall of the guide opening. In this form of the invention the lateral area of the guide opening itself approximates the desired total area to be recessed.

In the integral guide means form of the invention, the guide bushing is first fixed in the operating position against the resected, osteotomized posterior surface of the patella and then a reamer tool is inserted into the guide opening. When the reamer tool is inserted, a portion of the guide surface abuts a portion of the reamer tool head or barrel and serves as a guide to fix the reamer tool in position within the total area to be recessed. The reamer tool can then be operated to produce a first round, intermediate recess. After operating the reamer tool to provide the initial round intermediate recess, the tool can be withdrawn and repositioned within the guide opening to cover a different area. The process of producing intermediate recesses is continued until the individual recesses combine to approximate the desired shape.

Alternatively to the guide means integrally formed with the guide bushing, the guide means may comprise a separate guide member or members, each adapted to be snugly received in the guide bushing opening. Each guide member includes a shaft opening for receiving the shaft of a rotary reamer tool. In this form of the invention, the guide member shaft opening fixes the position of the associated reamer tool within the guide bushing and within the total area to be recessed.

In the operation of this separate guide member form of the invention, the guide bushing is fixed in the operating position as discussed above and then the guide member with its associated rotary reamer tool is fixed in a guide position within the guide bushing opening. Once the guide member is in the guide position, the associated reamer tool may be operated to produce a round intermediate recess. After producing the initial intermediate recess, the guide member must be removed and repositioned within the guide bushing opening to position the associated reamer tool in a different reaming position. The process of producing intermediate recesses continues until the intermediate recesses combine to approximate the desired recess shape.

In the separate guide member form of the invention, the guide members may be adapted to be received in multiple positions within the guide bushing opening to fix the associated reamer tool in different reaming positions. Alternatively, or additionally, separate guide members and associated reamer tools may be required to produce the intermediate recesses necessary to approximate the total area to be recessed.

The apparatus according to the invention also includes guide bushing positioning means for positioning the guide bushing on the osteotomized patella and securing the guide bushing in the desired operating position. The positioning means preferably comprises superior and inferior clamp members extending parallel to each other, and a grip arrangement connected to both clamp members for controlling the distance between the clamp members. The superior clamp member includes a preferably U-shaped arrangement for receiving the guide bushing and a locking structure for locking the guide bushing onto the clamp member. A locking arrangement associated with the grip allows the clamp members to be positioned about the patella and locked in position securing the guide bushing in the desired operating position on the posterior surface of the osteotomized patella.

These and other objects, advantages, and features of the invention will be apparent from the following description of the preferred embodiments, considered along with the accompanying drawings.

DESCRIPTION OF THE PREFERRED EMBODIMENTS

Figure 1:
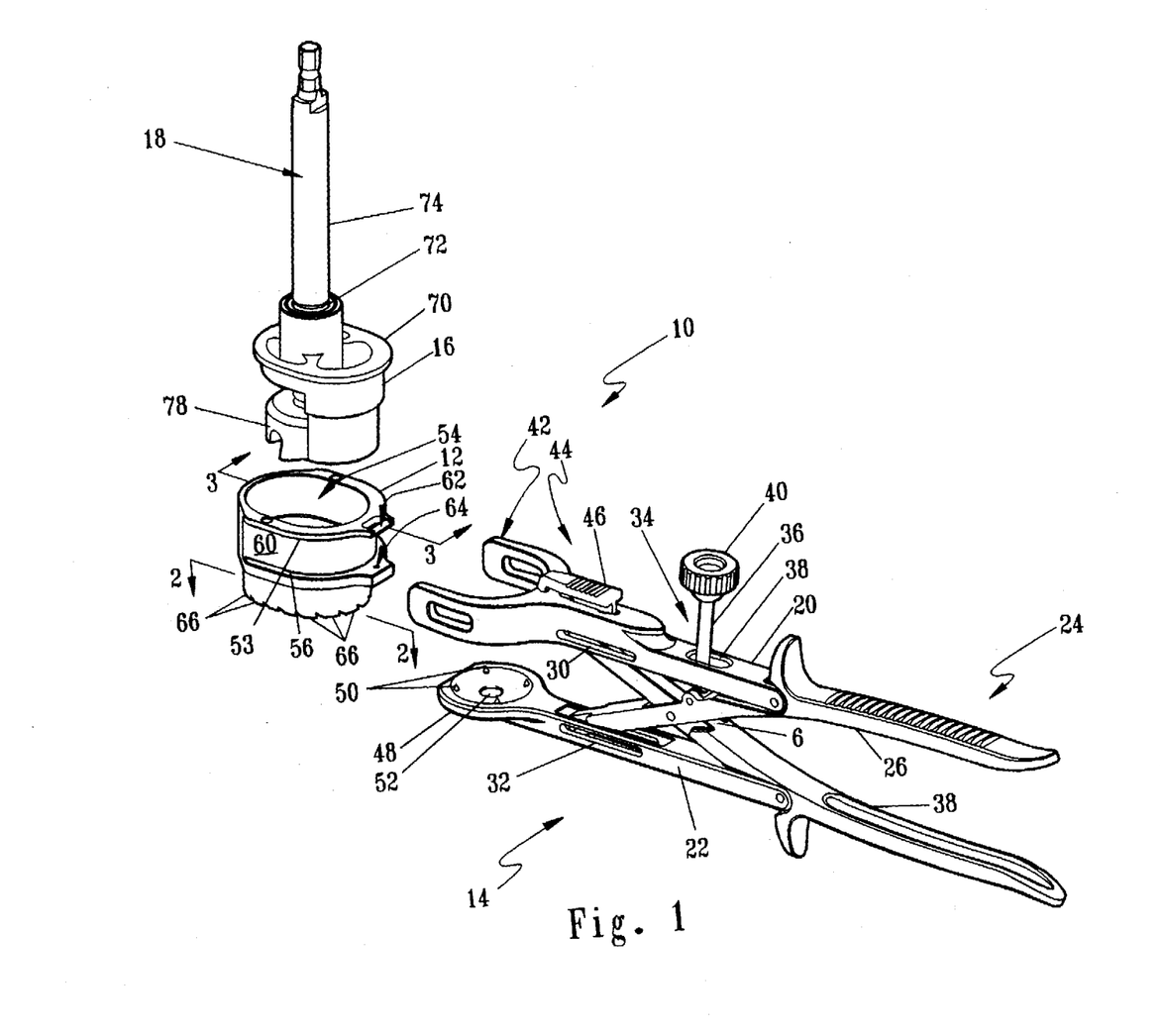
FIG. 1 is an exploded isometric drawing showing a patella recession instrument embodying the principle of the invention.

Referring to FIG. 1, the recession apparatus 10 according to the invention comprises a guide bushing 12, positioning means 14, and guide means, shown as a separate guide member 16 in the form of the invention illustrated in FIG. 1. The separate guide member 16 has associated with it a rotary reamer tool 18.

The guide bushing positioning means 14 preferably comprises a superior clamp member 20 and an inferior clamp member 22 both connected to a grip structure 24. The grip structure 24 includes a scissor arrangement comprising a first grip member 26 and a second grip member 28 pivotally connected about a pivot point G. The superior clamp member 20 is pivotally connected at one end to the first grip member 26 and connected through a slot and pivot arrangement 30 to an end of the second grip member 28. The inferior clamp member 22 is pivotally connected at one end to the second grip member 28 and connected through a pivot and slot arrangement 32 to the end of the first grip member 26. These connections allow the grip structure 24 to position the inferior clamp member 22 relative to the superior clamp member 20 and maintain the two clamp members parallel to each other throughout the range of movement imparted through the grip structure. The guide positioning means also includes a locking mechanism for locking the two clamp members 20 and 22 in the desired position parallel to each other about a patella (not shown). The illustrated locking mechanism includes a locking member 34 pivotally connected at one end to the first grip member 26 and having a threaded section 36 extending through an opening 38 formed in the superior clamp member 20. A locking nut 40 is positioned on the threaded portion 36 of the locking member 34 and is adapted to be threaded down to contact the superior clamp member 20 to lock the two clamp members 20 and 22 at a maximum separation distance.

The superior clamp member 20 includes a U-shaped structure 42 for receiving and holding the guide bushing 12. The U-shaped structure 42 is preferred because it can accommodate a number of different guide bushings having different interior dimensions. However, those skilled in the art will readily appreciate that the U-shaped guide bushing receiving structure 42 can be substituted with any suitable structure, including a closed ended structure for receiving the guide bushing 12 in the desired position on the superior clamp member 20. Regardless of the guide bushing receiving structure employed, the positioning means 14 also includes a bushing locking mechanism 44 connected to the superior clamp member 20 to contact a guide bushing 12 received in the receiving structure 42 and holding it in position on the superior clamp member. The bushing locking mechanism 44 can include any suitable locking mechanism and preferably includes a trigger member 46 pivotally connected to the superior clamp member 20 and adapted to itself contact the received guide bushing 12 and to position a locking member (not shown) to also contact the guide bushing when the guide bushing is received properly in the receiving structure 42.

The inferior clamp member 22 includes a stabilizing structure 48 adapted to grip the anterior surface of a patella (not shown) to help stabilize the guide bushing 12 in the desired operating position. The stabilizing structure 48 includes a series of projections 50 to help grip the anterior surface of the patella. Also, the stabilizing structure 48 preferably includes a measurement opening 52 in the center of the structure. The measurement opening 52 allows the surgeon to obtain accurate measurements from the anterior surface of the patella during the recession operation when the apparatus 10 is secured to the patella.

Figure 2:
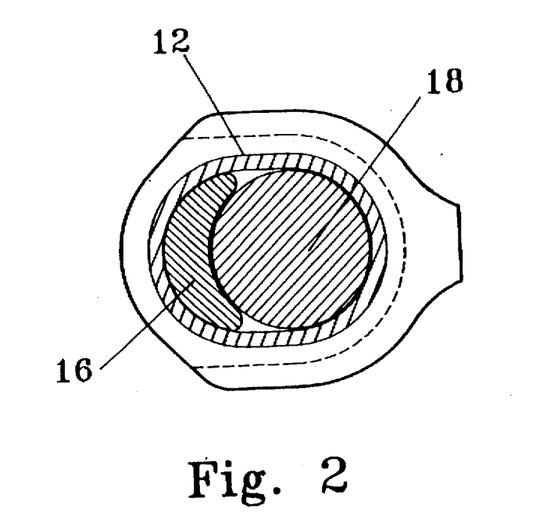
FIG. 2 is a view in section taken along line 2—2 in FIG. 1 but with the guide member and reamer in place.
Figure 3:
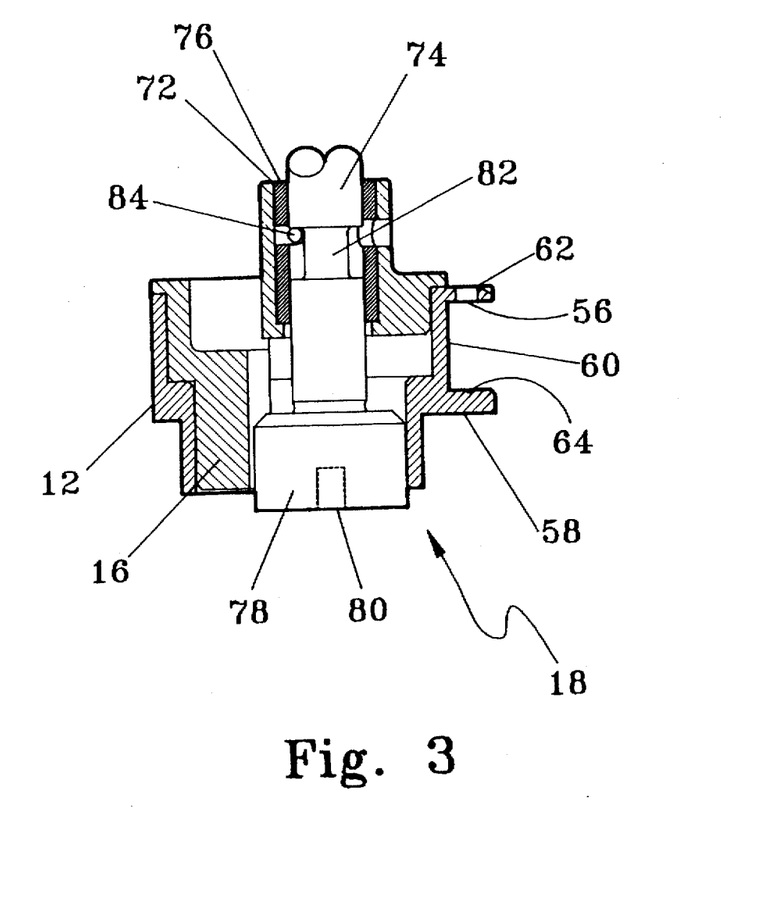
FIG. 3 is a view in section taken along line 3—3 in FIG. 1 but with the guide member and reamer in place.

Referring now to FIGS. 2 and 3 as well as FIG. 1, the guide bushing 12 has a generally oblong shape and includes a guide opening 54. The guide opening 54 in this form of the invention has a shape having a lateral extent that covers the total area of the patella to be recessed. The guide bushing 12 also includes a top connecting feature 56 and a lower connecting feature 58. The two connecting features 56 and 58 define a channel 60 on both longitudinal sides of the guide bushing exterior surface. The channel 60 is sized to snugly receive the arms of the U-shaped guide bushing receiving structure 42 formed on the superior clamp member 20 and allow the bushing 12 to be received in the U-shaped structure. A locking opening 62 on the top connecting feature cooperates with the locking trigger 46 mounted on the superior clamp member 20 to lock the bushing 12 in the desired position on the U-shaped structure 42. Also, an indent 64 may be formed in the lower connecting feature 58 of the guide bushing 12 and this indent may cooperate with another locking member (not shown) whose position is controlled by the locking trigger 46.

The lower face of the guide bushing 12 includes teeth 66 along at least a portion of the area. The teeth 66 serve to help grip the posterior osteotomized surface of the patella (not shown) to hold the bushing 12 in place in the desired operating position. In the illustrated form of the bushing and clamp structure, the contact with the patella is between the stabilizing structure 48 formed on the inferior clamp member 22 and the lower face of the guide bushing 12.

The guide means illustrated in FIGS. 1–3 comprises the separate guide member 16. The guide member 16 has a transverse cross-sectional shape allowing the device to be received snugly in the opening 54 of the guide bushing 12. A lip 70 formed on the top of the guide member 16 abuts the top of the guide bushing 12 when the guide member is inserted properly into the guide bushing opening 54 and serves as a stop for fixing the position of the guide member in the guide bushing.

The guide member 16 also includes a shaft opening 72 for receiving the elongated shaft 74 of the rotary reamer tool 18. The shaft receiving opening 72 may be lined with a suitable bearing surface 76 for supporting the shaft 74 of the rotary reamer tool 18 for rotation about the longitudinal axis of the shaft. The rotary reamer tool 18 also includes a tool head or barrel 78 having a cutting face 80 formed thereon. The rotary reamer tool 18 cuts a round opening as the tool is rotated about the longitudinal axis of the shaft 74. Also the shaft 74 includes a reduced diameter section 82. This reduced diameter section 82 cooperates with a pin 84 that may be fixed in the shaft receiving opening 72 of the guide member 16 to limit the movement of the rotary reamer tool 18 along its longitudinal axis and therefore limits the depth of the cut produced by the reamer tool. Also, the pin 84 may be removed to allow the rotary reamer tool 18 to be inserted into the shaft receiving opening 72 and removed therefrom as desired. However, when the rotary reamer tool 18 is received through the shaft receiving opening 72 of the guide member 16 and the pin 84 is in position, the rotary reamer tool is locked in position on the guide member.

The operation of the apparatus shown in FIGS. 1 and 3 and the method of the invention may now be described with reference to those figures. First, the guide bushing 12 is positioned in operating position adjacent the posterior osteotomized surface of the patella (not shown). In the operating position the opening 54 through the guide bushing 12 covers the entire or total area to be recessed on the patella.

Fixing the guide bushing 12 in the operating position in the form of the invention illustrated in FIGS. 1–3 includes first fixing the guide bushing in the U-shaped receiving structure 42 on the superior clamp member 20 and locking the guide bushing in position on the U-shaped bushing receiving structure. Once the guide bushing 12 is locked in place, the clamp members 20 and 22 are separated, using the grip structure 24 to enable the clamp members to be positioned around the patella to be recessed (not shown). After being positioned around the patella, the grip 24 is closed to position the stabilizing surface 48 of the inferior clamp member 22 adjacent the anterior surface of the patella and the teeth 66 of the guide bushing 12 gripping the posterior surface of the osteotomized patella. The locking nut 40 is then threaded down to contact the superior clamp member 20 to lock the clamp members and the guide bushing 12 in the desired operating position.

Once the guide bushing 12 is fixed in the operating position, the method of the invention includes sequentially positioning at least one rotary reamer tool 18 in a plurality of reaming positions within the opening 54 of the guide bushing, and then operating the rotary reamer tool 18 or tools to produce a series of intermediate recesses. In each different reaming position, the face of the rotary reamer tool 18 covers a different portion of the total area to be recessed. The different portions and intermediate recesses combine to approximate the total area to be recessed.

In the form of the invention where the guide means comprises a separate guide member 16, the step of sequentially positioning the rotary reamer tools 18 in different positions is performed with the guide member cooperating with the guide bushing 12. With the guide bushing 12 in the operating position the guide member 16, with its associated reamer tool 18 properly inserted in the reamer shaft opening 72 extending therethrough, is aligned with and then inserted into the opening 54 of the guide bushing. The off-center shaft position through the guide member 16 places the cutting face 80 of the rotary reamer tool 18 at one end of the elongated opening 54 through the guide bushing 12. After operating the reamer tool 18 in this position to produce a round intermediate recess (not shown) at one end of the elongated guide bushing opening 54, the guide member 16 is removed, the reamer tool 18 prepared for another cut, and then the guide member 16 is rotated 180 degrees and reinserted into the opening 54 of the guide bushing 12. In this position, the cutting face 80 of the reamer tool is positioned at the opposite end of the elongated guide bushing opening 54. Operating the reamer tool 18 in this position produces a second intermediate recess connected with the first intermediate recess and the two recesses now approximate the total oval area to be recessed.

It will be appreciated that the two spaced apart round recesses cut by the two different positions of the rotary reamer tool 18 described above will not produce a true oval shape but leave hubs (not shown) along the elongated side of the shape. These nubs may be removed by the surgeon or the implant (not shown) may displace the nubs as it is inserted into the recess.

Those skilled in the art will readily appreciate that a number of different recess shapes may be formed according to the invention. The invention may be used to produce any recessed shape that may be approximated by a plurality of overlapping circles. For example, in addition to the generally oval shape approximated by the device shown in FIGS. 1–3, the invention may be adapted to produce a tri-oval shape by positioning the reamer tool 18 in three different shaft positions. Also, an elliptical shape may be approximated according to the invention by a center large diameter recess and two smaller diameter recesses formed on both sides of the larger diameter recess, with the three shapes overlapping. Also, although the invention is discussed with respect to a patella and patellar implants, the invention is not limited to patellar recession. Rather, the invention of approximating oblong recession shapes may be applied to any recesses required for implants in orthopedic surgery.

Figure 4:
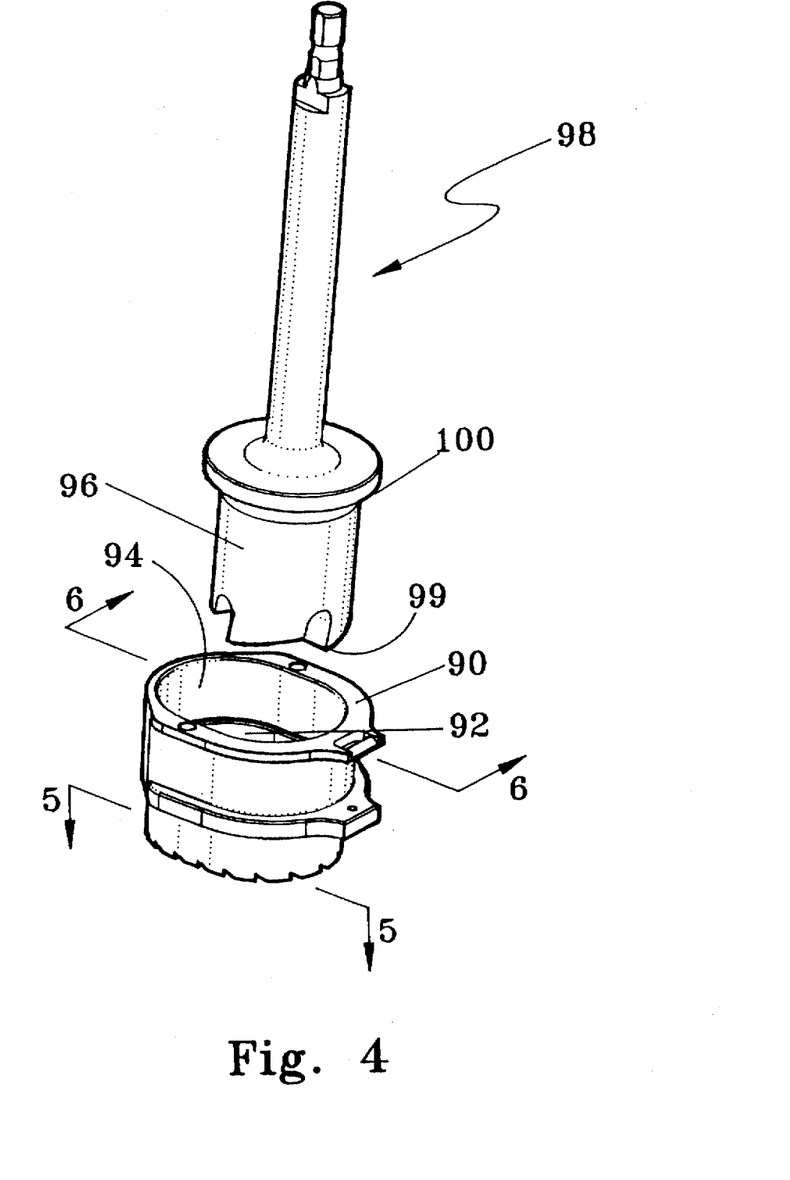
FIG. 4 is an exploded isometric drawing showing an alternative guide bushing have an integrally formed guide surface.
Figure 5:
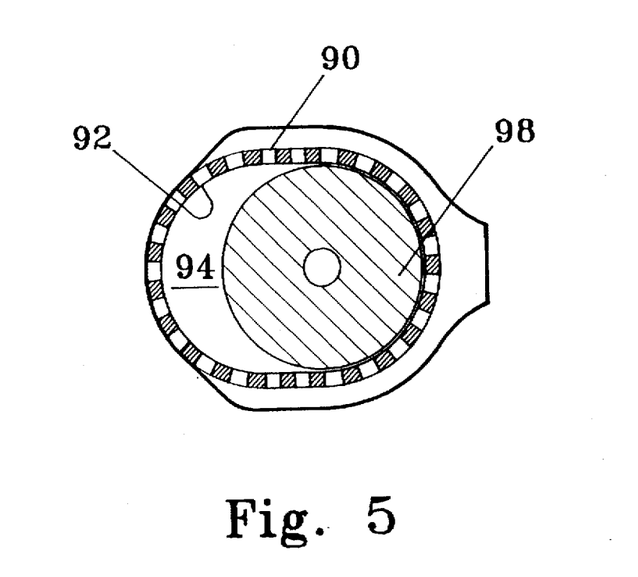
FIG. 5 is a view in section taken along line 5—5 in FIG. 4 but with the reamer inserted.
Figure 6:
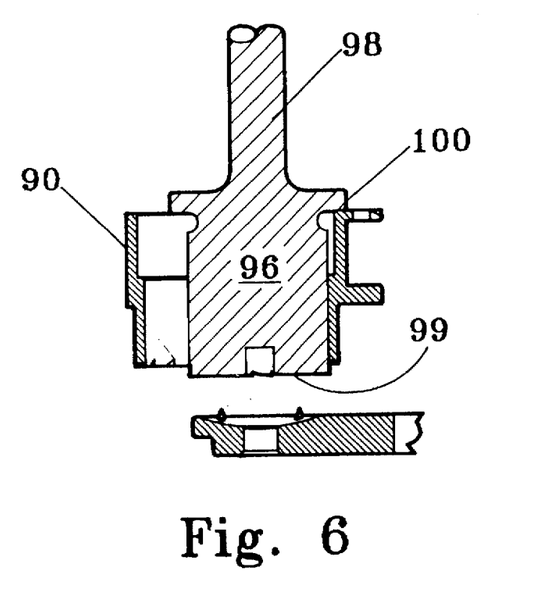
FIG. 6 is a view in section taken along line 6—6 in FIG. 4 but with the reamer inserted.

FIGS. 4, 5 and 6 show an alternative guide bushing 90 and reamer guide means according to the invention. In this form of the invention the reamer guide means is integrally formed with the guide bushing 90 rather than comprising a separate guide member. The reamer guide means in this form of the invention comprises simply the wall 92 of the guide bushing opening 94.

In the form of the invention shown in FIGS. 4, 5 and 6, the opening 94 of the guide bushing 90 itself approximates the total area to be recessed. The wall 92 of the guide bushing 90 cooperates with the barrel or cutting head 96 of the rotary reamer tool 98 to guide the rotary reamer tool in different reaming positions within the opening 94 of the guide bushing.

In operating the apparatus using the guide bushing 90 shown in FIGS. 4 and 5, the guide bushing 90 is fixed in an operating position similar to the guide bushing 12 described in FIGS. 1–3. After fixing the guide bushing 90 in the operating position, the rotary reamer tool 98 is inserted into the guide bushing opening 94 with the wall 92 of the guide bushing opening directing the position of the rotary reamer tool. The rotary reamer tool 98 may be positioned at one end of the guide bushing opening 94 and driven to produce a first round intermediate recess. The reamer tool 98 can then be withdrawn and repositioned at the opposite end of the guide bushing opening 94 and then driven to produce a second intermediate recess. At this point the two overlapping circular shapes defined by the radius of the rotary reamer tool cutting face 99 may sufficiently define the desired recess, leaving nubs as discussed above with reference to FIGS. 1–3. However, in this form of the invention the guide opening 94 through the guide bushing 90 is a true oval shape, and thus the rotary reamer tool 98 is not restricted to only two positions through the guide opening. In this form of the invention the rotary reamer tool 98 may be withdrawn and repositioned after the second cut one or more times to remove the nubs to the desired level. During each cut, a lip 100 at the top of the rotary reamer tool cutting head 96 serves to limit the depth of the cut that may be made by the rotary reamer tool 98 through the guide bushing opening 94.

Figure 7:
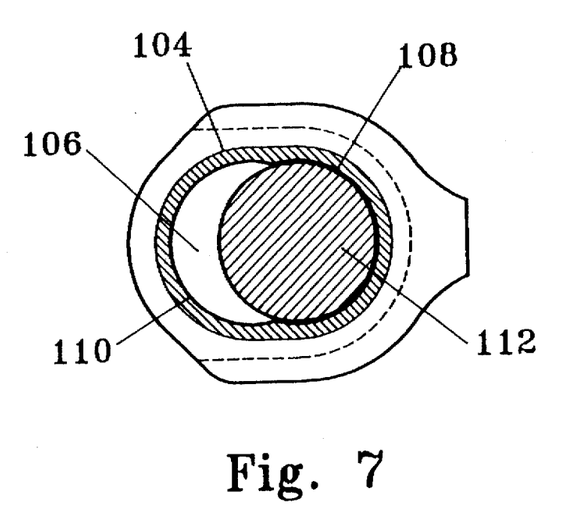
FIG. 7 is a view in section similar to FIG. 5 showing another alternative form of the guide bushing according to the invention.

FIG. 7 shows yet another alternative form of the guide bushing 104 according to the invention with integrally formed reamer guide means. This form of the invention is similar to that shown in FIGS. 4 and 5 except that the guide opening 106 through the guide bushing 104 comprises two intersecting circular shapes 108 and 110. The rotary reamer tool 112 in this form of the invention may be received only in two positions through the guide bushing opening 106 and will leave nubs as discussed with FIGS. 1–3. However, the shape produced by the overlapping circles 108 and 110 even with the nubs, is sufficient to approximate the desired oval shaped recess for receiving an oval shaped patellar implant. The nubs may be removed with an unguided reamer tool or may be displaced as the implant is inserted into the recess.

The above described preferred embodiments are intended to illustrate the principles of the invention, but not to limit the scope of the invention. Various other embodiments and modifications to these preferred embodiments may be made by those skilled in the art without departing from the scope of the following claims.

Figure 8:
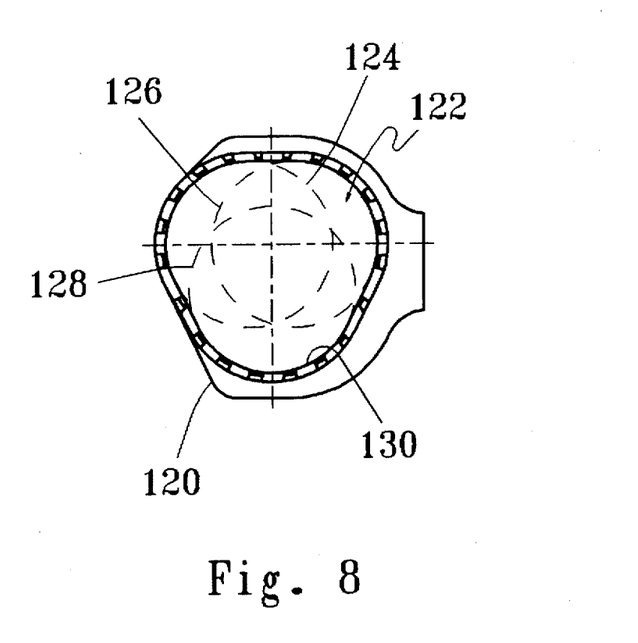
FIG. 8 is a bottom view showing another alternate form of the reamer guide according to the invention.

FIG. 8 shows another alternate form of the guide bushing 120. In this form of the invention, the guide opening 122 encompasses three overlapping circular shapes 124, 126, and 128. The three overlapping circular shapes 124, 126, and 128 form generally a tri-oval. To produce the desired tri-oval recess with the guide bushing 120 a rotary reamer tool (not shown in FIG. 8) is positioned in three different locations, each location corresponding to one of the circular shapes 124, 126, and 128. In this embodiment of the invention, the reamer guide means comprises the wall 130 of the guide bushing opening 122.

We claim:

1. An apparatus employing a plurality of rotary reamer tools for producing a recess in the posterior surface of a patella for receiving a patellar implant, the apparatus comprising:

(a) a guide bushing having a guide opening therethrough;
   (b) bushing positioning means for positioning and securing the guide bushing against the posterior surface of the patella in an operating position with the guide opening covering a total area of the patella to be recessed; and
   (c) reamer guide means associated with the guide bushing, the reamer guide means for fixing a cutting face of each rotary reamer tool in at least one reaming position with the total area to be recessed when the guide bushing is in the operating position, the cutting face of the rotary reaming tool in each different position covering a different portion of the total area to be recessed, and such different portions combining to approximate an oblong area.

2. The apparatus of claim 1 wherein the reamer guide means includes:

(a) at least one reamer guide member, each reamer guide member having a transverse cross-sectional shape enabling it to be received snugly in a guide position within the guide opening of the guide bushing; and
   (b) a shaft opening in each reamer guide member extending substantially parallel with the guide opening of the guide bushing when said reamer guide member is positioned in the guide position, the shaft opening for receiving a shaft of one of said rotary reamer tools and determining the reaming position of said rotary reamer tool received therein when said reamer guide member is received in the guide position and the guide bushing is received in the operating position.

3. The apparatus of claim 2 wherein each reamer guide member includes a stop structure associated with the reamer shaft opening therein, the stop structure for controlling the depth to which one of said rotary reamer tools may be inserted through the shaft opening.

4. The apparatus of claim 2 wherein:

(a) the recess for receiving the patellar implant is substantially oval-shaped;
   (b) the reamer guide means includes a single reamer guide member; and
   (c) the single reamer guide member may be received in a first and a second guide position within the guide opening of the guide bushing.

5. The apparatus of claim 1 wherein: (a) the recess for receiving the patellar implant is substantially tri-oval shaped.

6. The apparatus of claim 1 wherein the reamer guide means comprises:

(a) a guide surface formed within the guide opening of the guide bushing, the guide surface extending substantially perpendicularly with respect to the posterior surface of the patella when the guide bushing is in the operating position and substantially defining the total area to be recessed.

7. The apparatus of claim 1 wherein the bushing positioning means includes:

(a) an inferior clamp member;
   (b) a superior clamp member;
   (c) grip means to which both the inferior clamp member and the superior clamp member are connected, the grip means for controlling the position of the inferior and superior clamp members with respect to each other;
   (d) a guide bushing receiving structure formed on the superior clamp member for receiving the guide bushing and locking the guide bushing in place with respect to the superior clamp member; and (e) locking means associated with the grip means for locking the inferior and superior clamp members in a spaced apart position gripping the patella to be recessed, with the inferior clamp member adjacent to the anterior side of the patella and the superior clamp member, and the guide bushing received therein adjacent to the posterior side of the patella.

8. The apparatus of claim 7 wherein the guide bushing receiving structure comprises:

(a) a U-shaped structure formed on a distal end of the superior clamp member; and (b) bushing locking means associated with the superior clamp member for contacting a portion contacting a portion of the guide bushing received in the U-shaped structure and locking the guide bushing in position with respect to the U-shaped structure.

9. An apparatus for producing a recess in the posterior surface of a patella for receiving a patellar implant, the apparatus comprising:

(a) a guide bushing having a guide opening therethrough;

(b) bushing position means for positioning and securing the guide bushing against the posterior surface of the patella in an operating position in which the guide opening covers a total area to be recessed;

(c) a rotary reamer tool having an elongated shank and a cutting head with a cutting face formed thereon; and (d) reamer guide means associated with the guide bushing, the reamer guide means for fixing the cutting face of the rotary reamer tool in a plurality of reaming positions within the total area to be recessed when the guide bushing is in the operating position, the cutting face of the rotary reamer tool in each different reaming position covering a different portion of the total area to be recessed and such different portions combining to approximate an oblong area.

10. The apparatus of claim 9 wherein the reamer guide means includes:

(a) at least one reamer guide member, each reamer guide member having a transverse cross-sectional shape enabling it to be received snugly in a guide position within the guide opening of the guide bushing; and (b) a shaft opening in each reamer guide member extending substantially parallel with the guide opening of the guide bushing when said reamer guide member is positioned in the guide position, the shaft opening for receiving the shaft of the rotary reamer tool and determining the reaming position of the rotary reamer tool received therein when said reamer guide member is received in the guide position and the guide bushing is received in the operating position.

11. The apparatus of claim 10 wherein each reamer guide member includes a stop structure associated with the reamer shaft opening therein, the stop structure for controlling the depth to which the rotary reamer tool may be inserted through the shaft opening.

12. The apparatus of claim 10 wherein:

(a) the recess for receiving the patellar implant is substantially oval-shaped;

(b) the reamer guide means includes a single reamer guide member; and (c) the single reamer guide member may be received in a first and second guide position within the guide opening of the guide bushing.

13. The apparatus of claim 9 wherein the reamer guide means comprises:

(a) a guide surface formed within the guide opening of the guide bushing, the guide surface extending substantially perpendicularly to the posterior surface of the patella when the guide bushing is in the operating position and substantially defining the total area to be recessed.

14. The apparatus of claim 9 wherein the bushing positioning means includes:

(a) an inferior clamp member;

(b) a superior clamp member;

(c) grip means to which both the inferior clamp member and the superior clamp member are connected, the grip means for controlling the position of the inferior and superior clamp members with respect to each other;

(d) a guide bushing receiving structure formed on the superior clamp member for receiving the guide bushing and locking the guide bushing in place with respect to the superior clamp member; and (e) locking means associated with the grip means for locking the inferior and superior clamp members in a spaced apart position gripping the patella to be recessed, with the inferior clamp member adjacent to the anterior side of the patella and the superior clamp member, and the guide bushing received therein, adjacent to the posterior side of the patella.

15. The apparatus of claim 14 wherein the guide bushing receiving structure comprises:

(a) a U-shaped structure formed on a distal end of the superior clamp member; and (b) a bushing locking means associated with the superior clamp member for contacting a portion of the guide bushing received in the U-shaped structure and locking the guide bushing in position with respect to the U-shaped structure.

16. A method for producing a patellar recess for receiving an anatomically shaped patellar implant, the method comprising the steps of:

(a) securing a guide bushing in an operating position against the posterior surface of the patella to be recessed, the guide bushing having a guide opening therethrough and the guide opening covering a total area to be recessed when the guide bushing is secured in the operating position;

(b) sequentially positioning at least one rotary reamer tool in a plurality of different reaming positions within the guide opening of the guide bushing; and (c) during the time that each rotary reamer tool is positioned in the respective reaming position, driving the rotary reamer tool to produce a separate intermediate recess in the patella, the separate intermediate recesses combining to form a continuous oblong recess approximating the total area to be recessed.

17. The method of claim 16 wherein the step of sequentially positioning at least one rotary reamer tool includes the step of:

(a) sequentially positioning at least one reamer guide member in a plurality of guide positions within the guide opening of the guide bushing, each reamer guide member having a reamer shaft opening therethrough for receiving the shaft of a rotary reamer tool, and each reamer guide member fixing the position of the rotary reamer associated therewith within the total area to be recessed.

18. The method of claim 16 wherein the step of sequentially positioning at least one reamer guide member in the guide opening of the guide bushing comprises the steps of:

(a) positioning a first reamer guide member in a first guide position within the guide bushing opening in which first guide position the rotary reamer tool associated with the first reamer guide member is aligned in a first reaming position;

(b) removing the first reamer guide member from the first guide position; and (c) repositioning the first reamer guide member in a second guide position within the guide bushing opening, in which second guide position the rotary reamer tool associated with the first guide member is aligned in a second reaming position.

19. The method of claim 18 wherein the step of sequentially positioning at least one guide member in the guide opening of the guide bushing further includes:

(a) removing the first reamer guide member from the second guide position;

(b) positioning a second rotary reamer tool in a third guide position within the opening of the guide bushing, in which third guide position the second rotary reamer tool is aligned in a third reaming position.

20. The method of claim 16 wherein the step of securing the guide bushing in the operating position comprises:

(a) securing the guide bushing to a superior clamp member; and (b) clamping the patella between the guide busing and an inferior clamp member with the guide bushing adjacent the posterior surface of the patella and the inferior clamp member adjacent the anterior surface of the patella.

* * * * *

UNITED STATES PATENT AND TRADEMARK OFFICE
CERTIFICATE OF CORRECTION

PATENT NO. : 5,716,360  
DATED : February 10, 1998  
INVENTOR(S) : James L. Baldwin, et al.

Page 1 of 3

It is certified that error appears in the above-indentified patent and that said Letters Patent is hereby corrected as shown below:

Title page, item [54], and column 1, line 1, in the title

Change "RECESSION" to --RESECTION--.

In the Abstract:

Line 1, change "recession" to --resection--.

Line 16, change "recession" to --resection--.

Column 3, line 30, change "recession" to --resection--.

Column 3, line 30, change "principle" to --principles--.

Column 3, line 53, change "recession" to --resection--.

Column 4, line 51, change "recession" to --resection--.

Column 6, line 40, change "hubs" to --nubs--.

Column 6, line 44, change "an" to --art--.

Column 6, line 58, change "recession" to --resection--.

UNITED STATES PATENT AND TRADEMARK OFFICE
CERTIFICATE OF CORRECTION

PATENT NO. : 5,716,360
DATED : February 10, 1998
INVENTOR(S) : James L. Baldwin, et al.

It is certified that error appears in the above-identified patent and that said Letters Patent is hereby corrected as shown below:

Column 6, line 59, change "recession" to --resection--.

Column 6, line 61, after the number "5", add a --,--.

Column 7, line 50, change "an" to --art--.

Column 7, move the paragraph starting at line 46 beginning with "The above described preferred embodiments..." and ending with "...of the following claims." to follow the next paragraph which begins with "FIG. 8..." and ends with "...bushing opening 122."

Column 8, line 10, change "with" to --within--.

Column 8, line 44, begin a new paragraph at --(a)--.

Column 8, line 67, change "damp" to --clamp--.

UNITED STATES PATENT AND TRADEMARK OFFICE
CERTIFICATE OF CORRECTION

PATENT NO.  : 5,716,360
DATED       : February 10, 1998
INVENTOR(S) : James L. Baldwin, et al.

It is certified that error appears in the above-indentified patent and that said Letters Patent is hereby corrected as shown below:

Column 9, line 13, at the end of the line delete the words "contacting a".

Column 9, line 14, at the beginning of the line delete the word "portion".

Signed and Sealed this

Twenty-third Day of June, 1998

Attest:

BRUCE LEHMAN

*Attesting Officer*    *Commissioner of Patents and Trademarks*